(12) United States Patent
Takahashi et al.

(10) Patent No.: US 11,759,098 B2
(45) Date of Patent: Sep. 19, 2023

(54) ENDOSCOPE APPARATUS AND OPERATING METHOD OF ENDOSCOPE APPARATUS

(71) Applicant: OLYMPUS CORPORATION, Tokyo (JP)

(72) Inventors: Jumpei Takahashi, Tokyo (JP); Ryosuke Ito, Hino (JP); Yohei Tanikawa, Hino (JP); Takayuki Tsukagoshi, Hino (JP); Yuki Shono, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 570 days.

(21) Appl. No.: 17/086,527

(22) Filed: Nov. 2, 2020

(65) Prior Publication Data

US 2021/0076922 A1 Mar. 18, 2021

Related U.S. Application Data

(63) Continuation of application No. PCT/JP2018/019038, filed on May 17, 2018.

(51) Int. Cl.
*A61B 1/06* (2006.01)
*A61B 1/045* (2006.01)
(Continued)

(52) U.S. Cl.
CPC ........ *A61B 1/0638* (2013.01); *A61B 1/00006* (2013.01); *A61B 1/000094* (2022.02);
(Continued)

(58) Field of Classification Search
None
See application file for complete search history.

(56) References Cited

U.S. PATENT DOCUMENTS

| 8,531,512 B2 | 9/2013 | Gono et al. |
| 2003/0176768 A1* | 9/2003 | Gono ........... A61B 1/0669 |
| | | 600/109 |

(Continued)

FOREIGN PATENT DOCUMENTS

| JP | 2006-068113 A | 3/2006 |
| JP | 2016-67775 A | 5/2016 |

(Continued)

OTHER PUBLICATIONS

International Search Report dated Aug. 7, 2018 issued in PCT/JP2018/019038.

*Primary Examiner* — John P Leubecker
*Assistant Examiner* — Jae K. Woo
(74) *Attorney, Agent, or Firm* — Scully, Scott, Murphy & Presser, P.C.

(57) ABSTRACT

An endoscope apparatus including: a light source configured to emit illumination light including light in a first wavelength band included in a blue wavelength band, light in a first narrowband included in a green wavelength band, and light in a second narrowband having a same light absorption coefficient of hemoglobin as that of the light in the first narrowband; an imager configured to acquire a first image of an object in the first wavelength band, a first narrowband image of the object in the first narrowband, and a second narrowband image of the object in the second narrowband; and a processor including hardware. The processor is configured to implement acquiring scattering characteristics information based on a comparison result between the first narrowband image and the second narrowband image, and generating an observation image using the first image, the first narrowband image, and the scattering characteristics information.

20 Claims, 9 Drawing Sheets

(51) Int. Cl.
*A61B 1/00* (2006.01)
*A61B 1/05* (2006.01)

(52) U.S. Cl.
CPC ............... *A61B 1/045* (2013.01); *A61B 1/05* (2013.01); *A61B 1/0655* (2022.02); *A61B 1/0661* (2013.01)

(56) References Cited

U.S. PATENT DOCUMENTS

| | | | | |
|---|---|---|---|---|
| 2006/0241349 | A1* | 10/2006 | Gono | A61B 1/0638 600/160 |
| 2007/0153542 | A1* | 7/2007 | Gono | A61B 1/000094 362/574 |
| 2012/0154567 | A1* | 6/2012 | Yamaguchi | A61B 1/000094 348/E7.085 |
| 2013/0041267 | A1* | 2/2013 | Ntziachristos | A61B 5/0068 600/476 |
| 2013/0053703 | A1* | 2/2013 | Yamamoto | A61B 1/0653 600/476 |
| 2013/0265401 | A1* | 10/2013 | Igarashi | A61B 1/0661 348/68 |
| 2013/0293693 | A1* | 11/2013 | Igarashi | A61B 1/000094 348/70 |
| 2015/0099932 | A1* | 4/2015 | Morimoto | A61B 1/00057 315/153 |
| 2016/0089010 | A1* | 3/2016 | Aoyama | A61B 1/0005 348/70 |
| 2016/0089012 | A1* | 3/2016 | Aoyama | H04N 23/74 348/71 |
| 2016/0174886 | A1* | 6/2016 | Shiraishi | A61B 5/14503 600/339 |
| 2018/0279853 | A1 | 10/2018 | Daidoji et al. | |
| 2019/0038111 | A1* | 2/2019 | Endo | A61B 1/0638 |
| 2019/0223705 | A1* | 7/2019 | Fukuda | G02B 23/2469 |
| 2021/0259515 | A1* | 8/2021 | Makino | A61B 1/07 |

FOREIGN PATENT DOCUMENTS

| | | |
|---|---|---|
| JP | 2017-192565 A | 10/2017 |
| JP | 2017-202241 A | 11/2017 |
| WO | 2017/051455 A1 | 3/2017 |

* cited by examiner

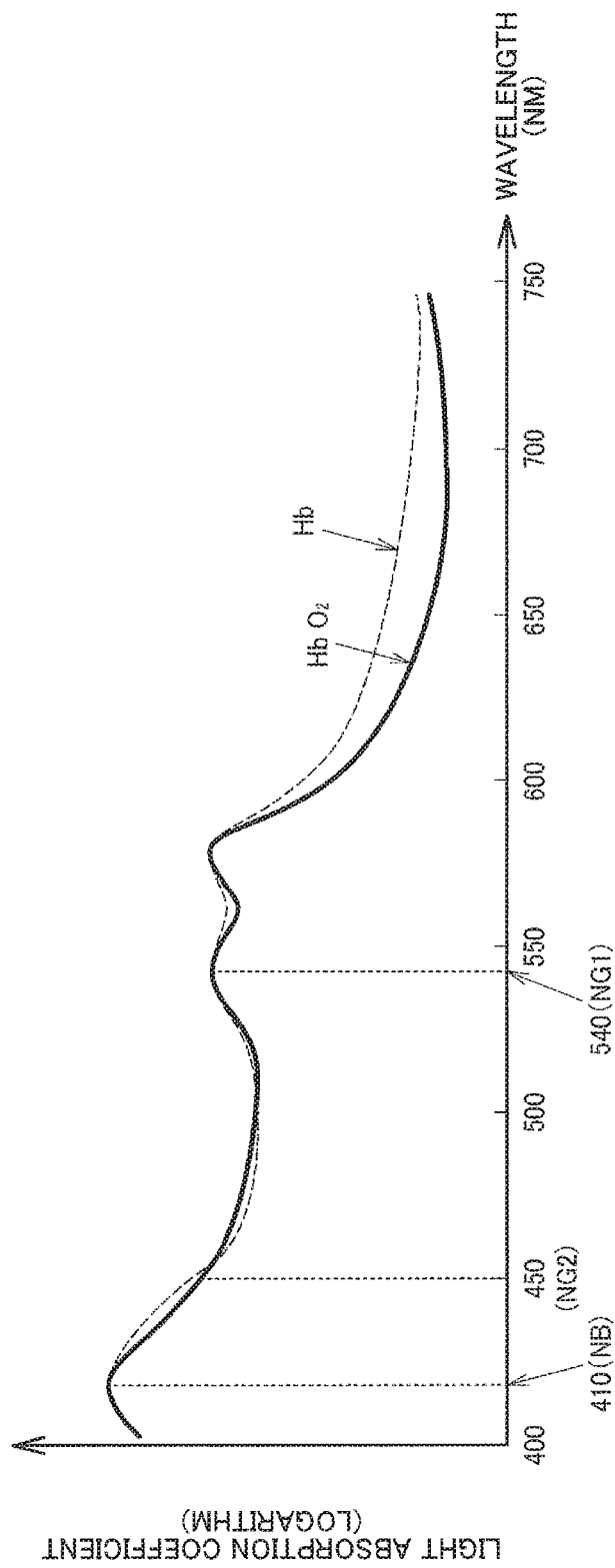

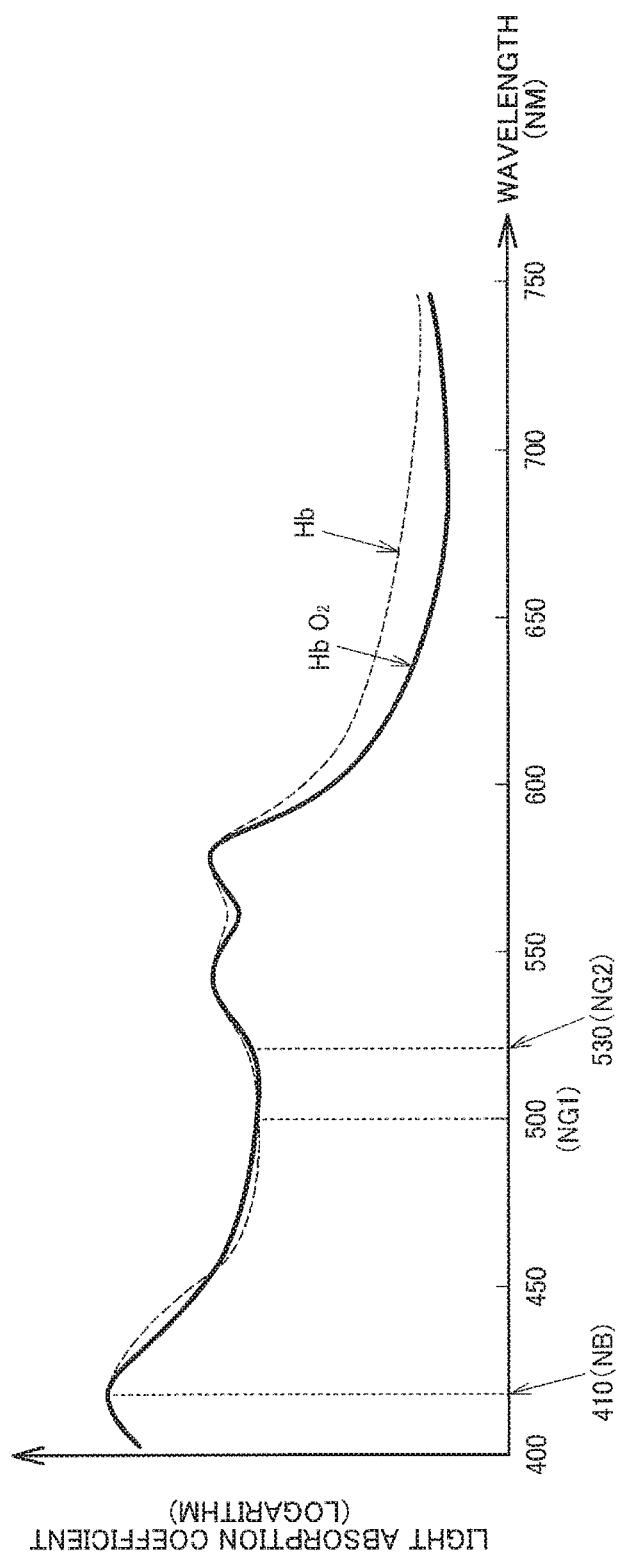

ENDOSCOPE APPARATUS AND OPERATING METHOD OF ENDOSCOPE APPARATUS

CROSS REFERENCE TO RELATED APPLICATION

This application is a continuation of International Patent Application No. PCT/JP2018/019038, having an international filing date of May 17, 2018, which designated the United States, the entirety of which is incorporated herein by reference.

BACKGROUND

An endoscope apparatus has been used to observe, for example, an inside of a digestive tract or a bladder. Moreover, narrow band imaging (NBI) has been known. NBI can improve visibility of an area including much hemoglobin by emitting illumination light of narrowband light having a high light absorption coefficient of hemoglobin on tissue. NBI shows inflammation and early-stage cancer as a brownish area (an area in a brownish color), which improves visibility of the inflammation and early-stage cancer. A technology of NBI is disclosed, for example, by JP-A-2006-68113.

SUMMARY

In accordance with one of the disclosure, there is provided an endoscope apparatus comprising:
a light source configured to emit illumination light including light in a first wavelength band included in a blue wavelength band, light in a first narrowband included in a green wavelength band, and light in a second narrowband having a same light absorption coefficient of hemoglobin as that of the light in the first narrowband;
an imager configured to capture an image of return light from an object that receives the illumination light so as to acquire a first image that is an image of the object in the first wavelength band, a first narrowband image that is an image of the object in the first narrowband, and a second narrowband image that is an image of the object in the second narrowband; and
a processor including hardware, the processor being configured to implement:
acquiring scattering characteristics information that is information about scattering characteristics of the object based on a comparison result between the first narrowband image and the second narrowband image; and
generating an observation image using the first image, the first narrowband image, and the scattering characteristics information.

According to another aspect of the disclosure, there is provided an operating method of an endoscope apparatus comprising:
emitting illumination light including light in a first wavelength band included in a blue wavelength band, light in a first narrowband included in a green wavelength band, and light in a second narrowband having a same light absorption coefficient of hemoglobin as that of the light in the first narrowband;
capturing an image of return light from an object that receives the illumination light so as to acquire a first image that is an image of the object in the first wavelength band, a first narrowband image that is an image of the object in the first narrowband, and a second narrowband image that is an image of the object in the second narrowband;
acquiring scattering characteristics information that is information about scattering characteristics of the object based on a comparison result between the first narrowband image and the second narrowband image; and
generating an observation image using the first image, the first narrowband image, and the scattering characteristics information.

BRIEF DESCRIPTION OF THE DRAWINGS

FIG. 10 is a graph illustrating a first modification example of narrowband light.
FIG. 11 is a graph illustrating a second modification example of narrowband light.

DESCRIPTION OF EXEMPLARY EMBODIMENTS

Figure 1:
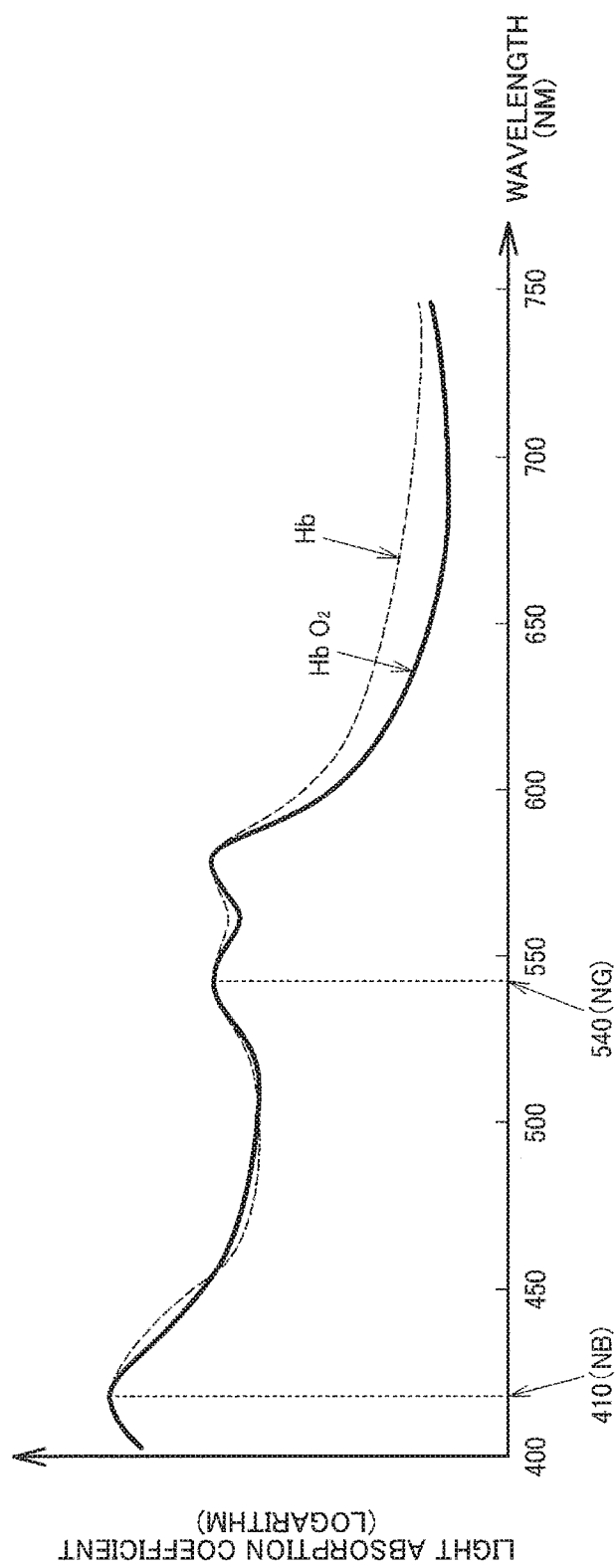
FIG. 1 is a graph illustrating a conventional NBI technology.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

1. Endoscope Apparatus

FIG. 1 is a graph illustrating a conventional NBI technology. In FIG. 1, Hb $O_2$ represents light absorption characteristics of oxidized hemoglobin and Hb represents light absorption characteristics of reduced hemoglobin. The light absorption characteristics are frequency characteristics of a light absorption coefficient.

As illustrated in FIG. 1, a light source of an endoscope apparatus emits narrowband light NB having a center wavelength of 410 nm and narrowband light NG having a center wavelength of 540 nm. For example, the narrowband light NB has a wavelength band from 390 to 445 nm, and the narrowband light NG has a wavelength band from 530 to 550 nm. Such narrowband light has characteristics of being easily absorbed into hemoglobin in blood. An imaging section of the endoscope apparatus captures an image of an object illuminated by the narrowband light NB and the narrowband light NG. For example, when a red-green-blue (RGB) image is captured using a color image sensor, an object image in the narrowband light NB is obtained as a B channel image, and an object image in the narrowband light NG is obtained as a G channel image. A B channel is input into a G channel and the B channel, and the G channel is input into an R channel, so as to generate an NBI image.

A light absorption coefficient of hemoglobin is larger at the wavelength of 410 nm than at the wavelength of 540 nm. Accordingly, an absorption amount of the narrowband light NB is relatively larger than an absorption amount of the narrowband light NG in an area of a blood vessel or the like having a high hemoglobin density. Since the object is imaged darkly at the wavelength having a high absorption amount, the G channel and the B channel are relatively darker than the R channel in the NBI image. Thus, the area of the blood vessel or the like having a high hemoglobin density appears brownish in the NBI image. The area appearing brownish is referred to as a brownish area. In a field of endoscope diagnosis, the NBI image implements highlighted display of a capillary in a mucous surface layer or a fine pattern of mucosa. The NBI image is used for diagnosis of cancer in the esophagus, large intestine, stomach or the like, for example.

However, the conventional NBI technology shows an area as the brownish area if the area has a high hemoglobin density. This makes it difficult to distinguish a brownish area of the cancer from a brownish area of other than the cancer in the NBI image. For example, an area where inflammation occurs in mucosa is sometimes shown as the brownish area in the NBI image. In such a case, both the areas of the inflammation and the cancer are highlighted as the brownish areas in the NBI image.

Figure 2:
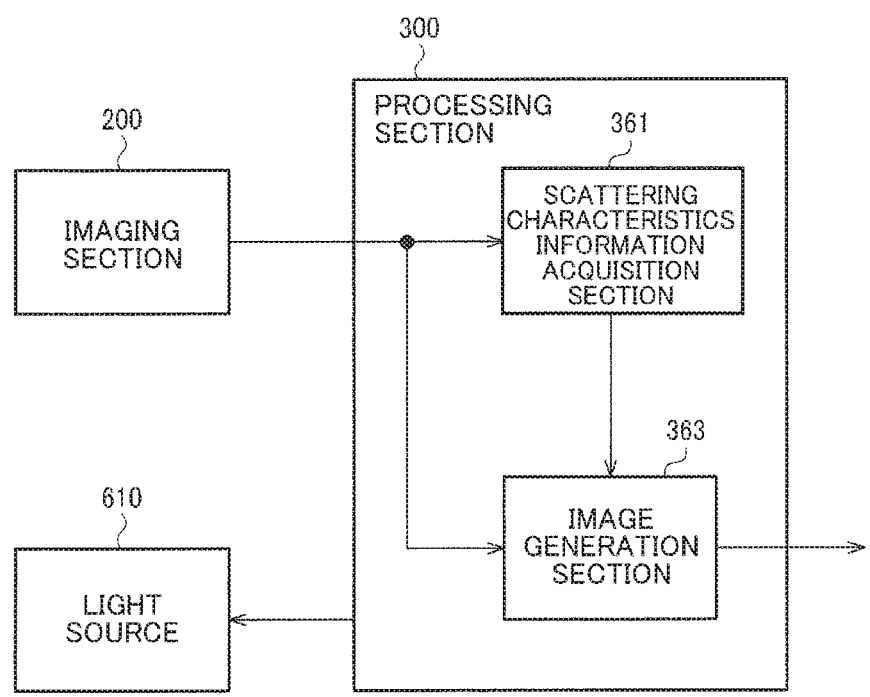
FIG. 2 is a configuration example of an endoscope apparatus.

FIG. 2 is a configuration example of an endoscope apparatus 12. The endoscope apparatus 12 includes a processing section 300, an imaging section 200, and a light source 610. The endoscope apparatus 12 is also referred to as an endoscope system. The processing section 300 is a processing device or a control device, for example. The imaging section 200 is an imager. The imaging section 200 may be detachable.

The light source 610 emits illumination light including first wavelength band light included in a blue wavelength band, first narrowband light included in a green wavelength band, and second narrowband light having the same light absorption coefficient of the hemoglobin as that of the first narrowband light. For example, in FIG. 4, the first wavelength band light corresponds to the narrowband light NB, the first narrowband light corresponds to narrowband light NG1, and the second narrowband light corresponds to narrowband light NG2.

The imaging section 200 captures an image of return light from the object that receives the illumination light. The imaging section 200 acquires a first image that is an image of the object in the first wavelength band, a first narrowband image that is an image of the object in the first narrowband, and a second narrowband image that is an image of the object in the second narrowband.

The processing section 300 includes a scattering characteristics information acquisition section 361 and an image generation section 363.

The scattering characteristics information acquisition section 361 acquires scattering characteristics information, which is information about scattering characteristics of the object, based on a comparison result between the first narrowband image and the second narrowband image. For example, in FIG. 4, a first narrowband image corresponds to an NG1 image, and a second narrowband image corresponds to an NG2 image. A pixel value of the NG1 image represents a scattering coefficient in the first narrowband, and a pixel value of the NG2 image represents a scattering coefficient in the second narrowband. Accordingly, the scattering characteristics information acquisition section 361 can acquire the scattering characteristics information by comparing the pixel values between the NG1 image and the NG2 image.

Figure 4:
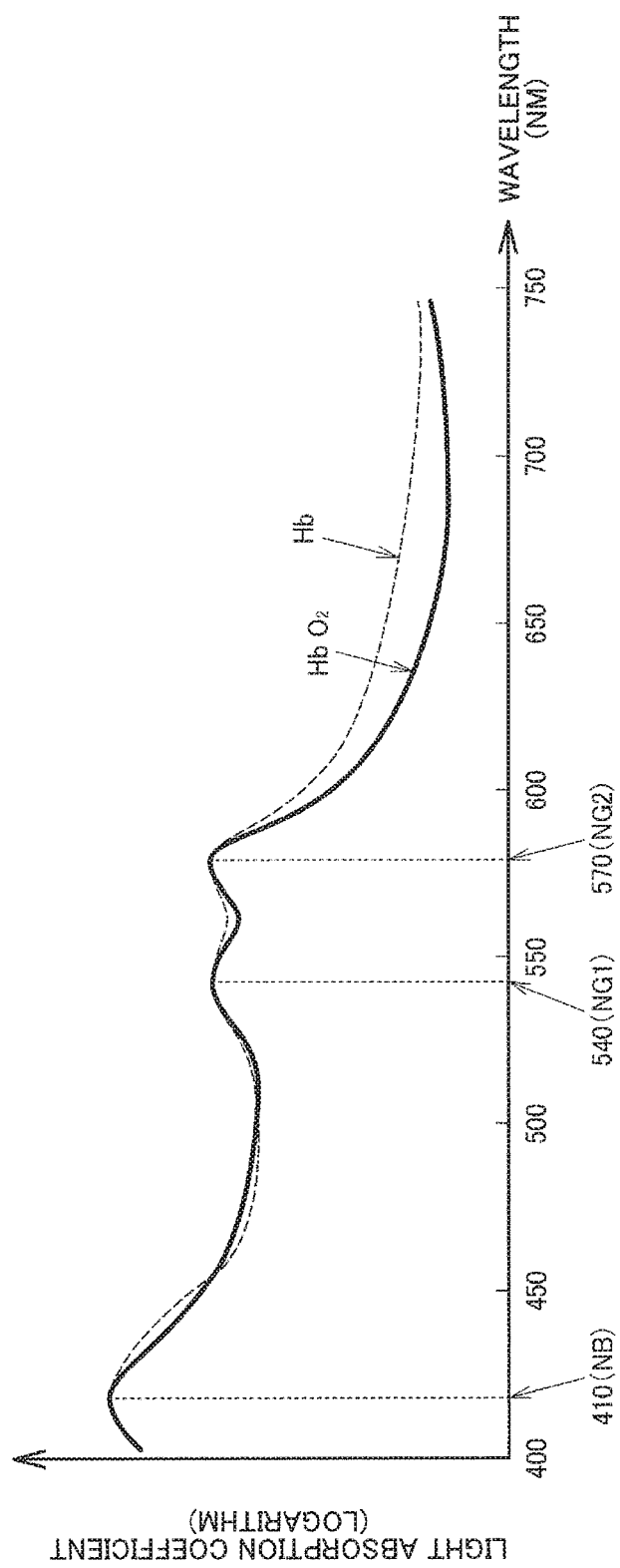
FIG. 4 is a graph illustrating narrowband light used in NBI observation in accordance with the present embodiment.

The image generation section 363 generates an observation image using the first image, the first narrowband image, and the scattering characteristics information. As will be described later in relation to steps S14 and S15 in FIG. 7, the image generation section 363 generates the observation image from an NB image and the NG1 image, performs a highlighting process on the observation image based on the scattering characteristics information, and outputs a resultant observation image after the highlighting process as a final observation image. In FIG. 4, the first image corresponds to the NB image.

As a result, in the present embodiment, generating the observation image using the first image (NB image) and the first narrowband image (NG1 image) enables generation of the NBI image as the observation image. Using the scattering characteristics information enables performing the highlighting process on the NBI image based on the scattering characteristics information. At this time, acquiring the scattering characteristics information based on the comparison result between the first narrowband image (NG1 image) and the second narrowband image (NG2 image) enables acquisition of a comparison result between the scattering coefficient in the first narrowband and the scattering coefficient in the second narrowband as the scattering characteristics information. Since the light absorption coefficients of the hemoglobin in the first narrowband and the second narrowband are the same, the scattering characteristics information can be acquired without being influenced by the hemoglobin. As will be described later referring to FIG. 6, a gradient of the scattering coefficient of early-stage cancer is larger than a gradient of an inflammation area. Accordingly, the scattering characteristics information differs in value between an area of the early-stage cancer and an area other than the early-stage cancer. Thus, performing the highlighting process on the observation image based on the scattering characteristics information can highlight the area of the early-stage cancer more than the area other than the early-stage cancer. As a result, the early-stage cancer and the inflammation area both displayed as the brownish areas in the NBI image can be distinguished by the highlighting process.

Furthermore, the scattering characteristics information acquisition section 361 acquires a change amount between the scattering characteristics in the first narrowband and the scattering characteristics in the second narrowband as the scattering characteristics information.

Figure 6:
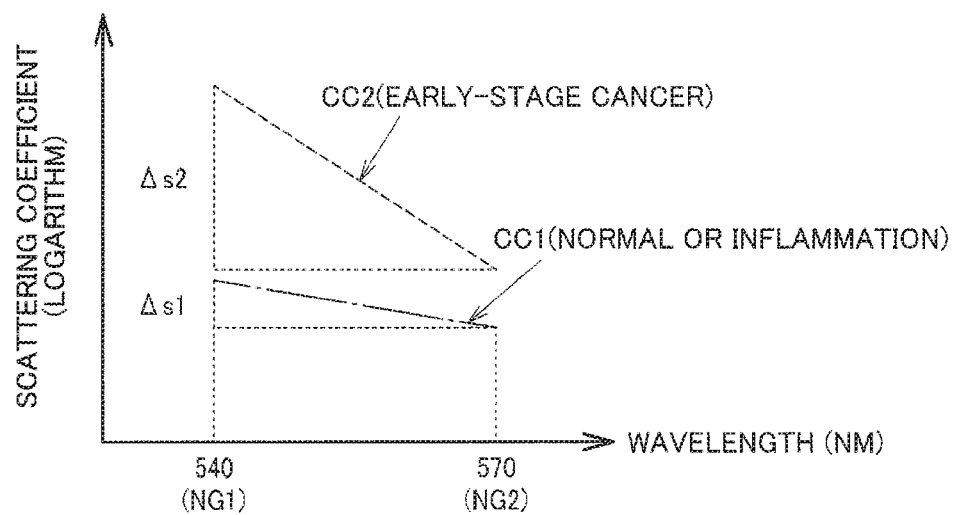
FIG. 6 is a graph illustrating a method for acquiring scattering characteristics information.

For example, in FIG. 6, a difference between the pixel value of the NG1 image and the pixel value of the NG2 image represents a gradient of the scattering coefficient. The gradient is the change amount between the scattering characteristics in the first narrowband and the scattering characteristics in the second narrowband. A gradient Δs2 of the early-stage cancer is larger than a gradient Δs1 of the inflammation area.

As a result, in the present embodiment, since the change amount between the scattering characteristics in the first narrowband and the scattering characteristics in the second narrowband is acquired, the highlighting process can be implemented on the observation image in accordance with the change amount. Since the change amount of the scattering characteristics differs between the early-stage cancer and the inflammation area, the early-stage cancer can be highlighted more than the inflammation area.

Furthermore, the scattering characteristics are scattering characteristics of a cell nucleus included in the object.

As will be described later referring to FIG. 5, Mie scattering using the cell nucleus as a scatterer is dominant in tissue. The scattering coefficient in the Mie scattering becomes larger as the scatterer becomes larger. Thus, acquiring the scattering characteristics information enables identification between the early-stage cancer and the inflammation area.

Furthermore, the scattering characteristics information acquisition section 361 acquires the scattering characteristics information based on a ratio between the pixel value of the first narrowband image and the pixel value of the second narrowband image.

As will be described later referring to a formula (1), the scattering characteristics information acquisition section 361 acquires the scattering characteristics information based on a ratio (PNG1/PNG2) between a pixel value PNG1 of the NG1 image and a pixel value PNG2 of the NG2 image.

As described above, the pixel value of the first narrowband image (NG1 image) represents the scattering coefficient in the first narrowband, and the pixel value in the second narrowband image (NG2 image) represents the scattering coefficient in the second narrowband. That is, the ratio between the pixel value of the first narrowband image and the pixel value of the second narrowband image is the change amount between the scattering characteristics in the first narrowband and the scattering characteristics in the second narrowband. Thus, the scattering characteristics information acquisition section 361 can acquire the scattering characteristics information based on the ratio between the pixel value of the first narrowband image and the pixel value of the second narrowband image.

Furthermore, the scattering characteristics information acquisition section 361 acquires the scattering characteristics information based on a subtraction result between the pixel value of the first narrowband image and the pixel value of the second narrowband image.

As will be described later referring to a formula (3), the scattering characteristics information acquisition section 361 acquires the scattering characteristics information based on a difference (PNG-PNG2) between the pixel value PNG1 of the NG1 image and the pixel value PNG2 of the NG2 image.

The subtraction result between the pixel value of the first narrowband image and the pixel value of the second narrowband image is the change amount between the scattering characteristics in the first narrowband and the scattering characteristics in the second narrowband. Thus, the scattering characteristics information acquisition section 361 can acquire the scattering characteristics information based on the subtraction result between the pixel value of the first narrowband image and the pixel value of the second narrowband image.

Furthermore, the scattering characteristics information acquisition section 361 performs a correction process on the first narrowband image and the second narrowband image, and acquires the scattering characteristics information based on a resultant first narrowband image and second narrowband image after the correction process.

Figure 7:
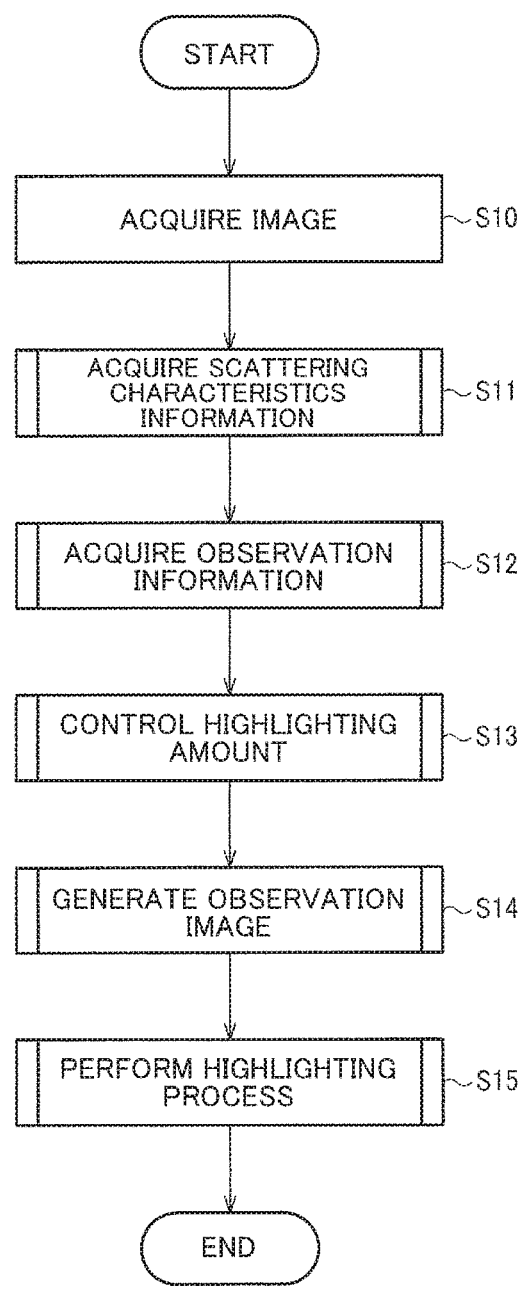
FIG. 7 is a flowchart illustrating procedures of processes performed by the endoscope apparatus.

The correction process is performed in a step S11 in FIG. 7, for example. The step S11 describes a process of acquiring the scattering characteristics information from the first narrowband image and the second narrowband image. The correction process is performed before this acquisition process on the first narrowband image and the second narrowband image.

For example, assume that the scattering characteristics information is degraded in quality by noise or the like in the first narrowband image and the second narrowband image. When this scattering characteristics information is used to perform the highlighting process, a resultant image after the highlighting process may be degraded in quality. In this regard, in the present embodiment, since the scattering characteristics information is acquired based on the first narrowband image and the second narrowband image after the correction process, the quality of the scattering characteristics information can be improved.

Furthermore, the correction process on the scattering characteristics information is a positioning process of positioning between the first narrowband image and the second narrowband image, or a brightness correction process of correcting brightness of the first narrowband image and the second narrowband image, or a noise reduction process of reducing the noise in the first narrowband image and the second narrowband image.

Timings for capturing the first narrowband image and the second narrowband image differ in a frame sequential method. When a scope or the object moves, a position shift occurs between the first narrowband image and the second narrowband image. The positioning corrects the position shift.

Furthermore, light adjustment control is performed in the endoscope apparatus 12 for maintaining the brightness of the image constant. The light adjustment control controls the brightness of the illumination light, and thus the brightness of the first narrowband image and the second narrowband image may differ. In addition, when the images are captured in the frame sequential method, the position shift may cause a difference in brightness between the first narrowband image and the second narrowband image. The light absorption coefficient of the hemoglobin is the same between the narrowband light NG1 and the narrowband light NG2. However, when the brightness of the images differs due to the above mentioned reasons, the scattering characteristics information is influenced by the hemoglobin, which prevents acquisition of accurate scattering characteristics information. In accordance with the present embodiment, the brightness of the first narrowband image and the second narrowband image is corrected to equalize the brightness of the first narrowband image and the second narrowband image. For example, average values of luminance values of the whole images are equalized. As a result, the scattering characteristics information not influenced by the hemoglobin can be acquired.

Furthermore, when the first narrowband image and the second narrowband image include the noise, the scattering characteristics information generated using these images also includes the noise. Performing the highlighting process based on this scattering characteristics information causes the noise in the highlighted area of the early-stage cancer or the like, for example. In accordance with the present embodiment, the noise in the first narrowband image and the second narrowband image is reduced to reduce the noise in the highlighted area. The noise reduction process is, for example, a low pass filter process to an image.

The scattering characteristics information acquisition section 361 acquires a scattering characteristics image having a pixel value equivalent to the change amount between the scattering characteristics in the first narrowband and the scattering characteristics in the second narrowband as the scattering characteristics information, and then performs the correction process on the scattering characteristics image. The image generation section 363 generates the observation image using the scattering characteristics image after the correction process.

The scattering characteristics image is an image having PSI in the formula (1), described later, as the pixel value, for example. The scattering characteristics image means that the scattering characteristics information is acquired at each position in two dimensions. That is, it means that the change amount is assigned to each pixel position in the observation image. The scattering characteristics image is data basically used for internal processing, and is not an image for display.

As a result, in the present embodiment, acquiring the scattering characteristics image of two-dimensional information enables acquisition of the scattering characteristics at each position in the images captured. Accordingly, the highlighting process can be performed on the area showing the scattering characteristics of the early-stage cancer based on the scattering characteristics information. Furthermore, the quality of the scattering characteristics image influences the highlighting process based on the scattering characteristics image. In accordance with the present embodiment, since the highlighting process is performed based on the scattering characteristics information after the correction process, the quality of the highlighting process can be improved.

Furthermore, the correction process on the scattering characteristics image is the noise reduction process of reducing the noise in the scattering characteristics image, or a binarization process of binarizing the scattering characteristics image.

Performing the highlighting process based on the scattering characteristics information including the noise causes the noise in the highlighted area of the early-stage cancer or the like, for example. In accordance with the present embodiment, the noise in the scattering characteristics image is reduced to reduce the noise in the highlighted area. The noise reduction process is, for example, the low pass filter process to the image.

In the binarization process, the pixel value is set to "1" when the pixel value of the scattering characteristics image is higher than a threshold value, and the pixel value is set to "0" when the pixel value of the scattering characteristics image is lower than the threshold value, for example. The values used for the binarization are not limited to 1 and 0. This process sets the pixel value in the area other than the early-stage cancer to "0", and thus the area other than the early-stage cancer is not highlighted. As a result, the area of the early-stage cancer can be clearly highlighted. In addition, since a highlighting amount is suppressed in the area other than the early-stage cancer, which does not need to be highlighted, an increase of the noise by the highlighting process can be prevented.

Furthermore, the image generation section 363 generates the observation image from the first image and the first narrowband image, and performs the highlighting process on the observation image by the highlighting amount controlled in accordance with hemoglobin content.

Specifically, as will be described later in relation to a step S13 in FIG. 7, a highlighting amount control coefficient is made larger as a ratio of an R pixel value/a G pixel value is higher. For example, an area having high hemoglobin content, such as an area having a high capillary density, is a brownish area having a high R. pixel value. Using the ratio of the R pixel value/the G pixel value as an index can make the highlighting amount in the area other than the brownish area relatively small. Highlighting the area other than the brownish area only increases the noise. Thus, suppressing the highlighting amount in the area other than the brownish area can reduce the noise.

Furthermore, the image generation section 363 makes the highlighting amount larger in an area having higher hemoglobin content in the observation image.

Figure 8:
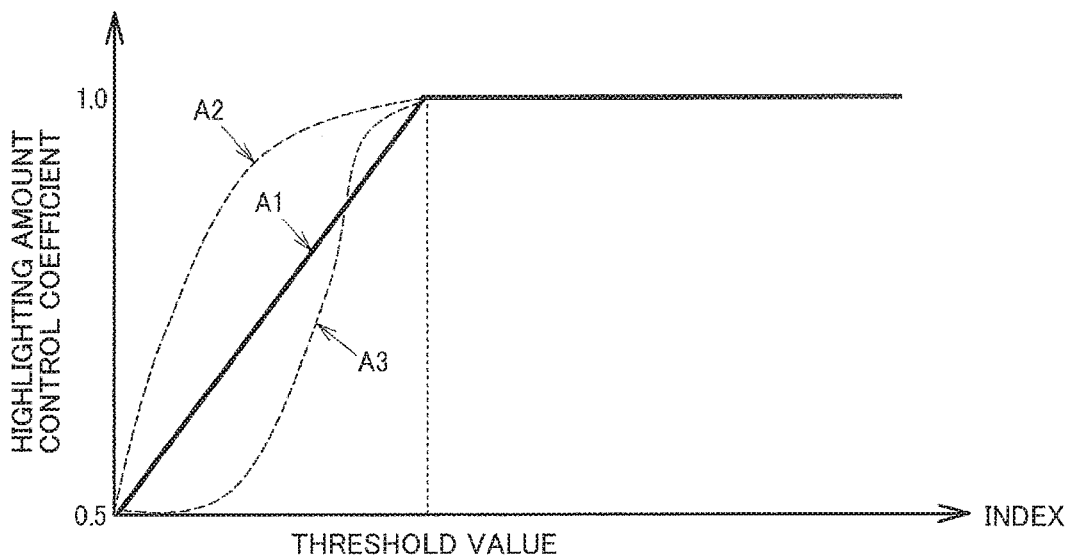
FIG. 8 is a graph illustrating a first characteristics example of a highlighting amount control coefficient.

As described above, the ratio of the R pixel value/the G pixel value becomes higher as the hemoglobin content becomes higher. As illustrated in FIG. 8, using the ratio of the R pixel value/the G pixel value as the index, the image generation section 363 makes the highlighting amount control coefficient larger as the index is higher, and multiplies the pixel value of the scattering characteristics image by a control amount control coefficient. As will be described later referring to a formula (7), the image generation section 363 performs the highlighting process using EAM that is a value obtained by multiplying the pixel value of the scattering characteristics image by the control amount control coefficient.

The area of the early-stage cancer desired to be highlighted is the brownish area and has the high hemoglobin content. Accordingly, the highlighting amount is made larger as the hemoglobin content in the area in the observation image becomes higher. As a result, the brownish area of the early-stage cancer can be highlighted. In addition, highlighting the area other than the brownish area can be relatively suppressed.

Furthermore, the image generation section 363 generates the observation image from the first image and the first narrowband image, and performs the highlighting process on the observation image by the highlighting amount or with content controlled in accordance with an observation scene.

The observation scene is, for example, an observation mode set to the endoscope apparatus, a state of the object in the image, or an observation method used by a user. A different observation scene requires different content or a different highlighting amount of the highlighting process. As a result, in the present embodiment, the highlighting process can be performed with appropriate content or by an appropriate highlighting amount in accordance with the observation scene.

Furthermore, the image generation section 363 generates the observation image from the first image and the first narrowband image, and performs the highlighting process with first content on the observation image in a first mode. The image generation section 363 generates a second observation image, which is an image of the object in a wavelength band of white light, and performs the highlighting process with second content different from the first content on the second observation image in a second mode.

The first mode is an NBI mode, and the observation image in the NBI mode is the NBI image. The second anode is a white light anode, and the observation image in the white light mode is a white light image. For example, a color (channel) to be highlighted is varied between the NBI mode and the white light mode. Alternatively, an area having a large scattering coefficient in the brownish area may be highlighted based on the scattering characteristics information in the NBI mode, and the highlighting process may be set to an OFF state in the white light mode. Alternatively, a different type of highlighting such as edge enhancement may be performed in the white light mode instead of highlighting of the brownish area. A different observation mode (illumination mode) requires different content or a different highlighting amount of the highlighting process. As a result, in the present embodiment, the highlighting process can be performed with appropriate content in accordance with the observation mode.

Furthermore, the image generation section 363 makes the highlighting amount smaller as a motion amount of the object is larger.

Figure 9:
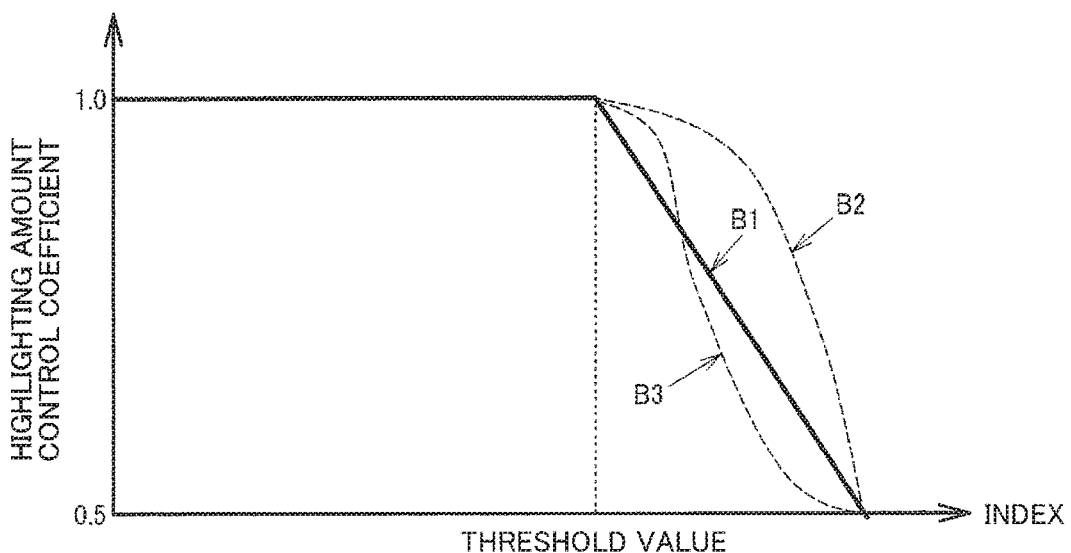
FIG. 9 is a graph illustrating a second characteristics example of a highlighting amount control coefficient.

Specifically, as illustrated in FIG. 9, using the motion amount between frames as the index, the image generation section 363 makes the highlighting amount control coefficient smaller as the index is higher, and multiplies the pixel value of the scattering characteristics image by the control amount control coefficient. As will be described later referring to the formula (7), the highlighting process is performed using EAM that is the value obtained by multiplying the pixel value of the scattering characteristics image by the control amount control coefficient.

When the motion of the object is large, a scene change is presumably occurring. Highlighting is hardly necessary during the scene change. In addition, the highlighting process increases the noise. As a result, in the present embodiment, since highlighting is suppressed when the motion amount of the object is large, the noise can be suppressed during the scene change.

Furthermore, the image generation section 363 makes the highlighting amount smaller in magnifying observation, in which the object is magnified for imaging, than the highlighting amount in observation other than the magnifying observation. In addition, the image generation section 363 may perform the noise reduction process of reducing the noise in the observation image in the magnifying observation.

As will be described later referring to FIG. 3, a focal distance can be known based on a focus control signal FDI that controls the focal distance of an objective lens. The focal distance is short in the magnifying observation. When it is determined that the focal distance is short based on the focus control signal FDI, it is determined that the magnifying observation is being performed. The magnifying observation is performed to carefully examine the object, and thus it is basically better not to perform highlighting. As a result, in the present embodiment, since the highlighting amount is reduced in the magnifying observation, visibility of the object during the careful examination can be improved. In addition, performing the noise reduction process can display an image with less noise in the magnifying observation.

Furthermore, the image generation section 363 makes the highlighting amount smaller in an area where an object other than tissue is imaged in the observation image than the highlighting amount in an area where the tissue is imaged in the observation image.

The object other than the tissue is, for example, a treatment tool. The tissue basically includes a small edge component, and the object other than the tissue includes relatively large edge component. Specifically, as illustrated in FIG. 9, using the edge component in the observation image as the index, the image generation section 363 makes the highlighting amount control coefficient smaller as the index is higher, and multiplies the pixel value of the scattering characteristics image by the control amount control coefficient. As will be described later referring to the formula (7), the highlighting process is performed using EAM that is the value obtained by multiplying the pixel value of the scattering characteristics image by the control amount control coefficient.

Since the brownish area is an area in the tissue, an area desired to be highlighted is a tissue area. As a result, in the present embodiment, since the highlighting amount is suppressed in the area where the object other than the tissue is imaged, highlighting can be suppressed in the area of the object other than the tissue that does not need to be highlighted.

Furthermore, the image generation section 363 performs the highlighting process on a specific channel image out of a plurality of channel images included in the observation image.

For example, formulas (6) to (8), described later, show the highlighting process performed on the image in the G channel. The specific channel is not limited to the G channel, but may be any one or two of the RGB channels.

Performing the highlighting process on the specific channel changes the color in the brownish area in accordance with the scattering characteristics information. Specifically, the color of the early-stage cancer having the high scattering coefficient changes. The inflammation area and the early-stage cancer appear as the same brownish area. However, changing the color of the early-stage cancer enables identification between the inflammation area and the early-stage cancer.

Furthermore, the image generation section 363 performs a color conversion process on the observation image based on the scattering characteristics information.

For example, as described above, the color is changed by multiplying the G channel by the scattering characteristics information. The color conversion process is not limited to this. For example, a hue of the observation image may be converted in accordance with the scattering characteristics information.

Performing the color conversion process based on the scattering characteristics information changes the color in the brownish area in accordance with the scattering characteristics information. Specifically, the color of the early-stage cancer having the high scattering coefficient changes. The inflammation area and the early-stage cancer appear as the same brownish area. However, changing the color of the early-stage cancer enables identification between the inflammation area and the early-stage cancer.

Furthermore, the first narrowband light is light having a wavelength with a maximum value of the light absorption coefficient of the hemoglobin.

For example, as illustrated in FIG. 4, one of two maximum values present in the green wavelength band is set as the first narrowband. The maximum value is a local largest value of the light absorption characteristics of the hemoglobin.

The NBI image is generated from the NB image (first image) and the NG1 image (first narrowband image). When the wavelength with the maximum value of the light absorption coefficient of the hemoglobin is set as the first narrowband, it is possible to generate the NBI image that largely changes in brightness relative to the hemoglobin content.

Furthermore, the first narrowband light is light having a wavelength of 540 nm. The second narrowband light is light having a wavelength of 570 or 450 nm.

FIG. 4 illustrates a case where the second narrowband has the wavelength of 570 nm. FIG. 10 illustrates a case where the second narrowband has the wavelength of 450 nm.

The light absorption coefficients of the hemoglobin at the wavelengths of 570 and 450 nm are the same as the light absorption coefficient of the hemoglobin at the wavelength of 540 nm. That is, setting these wavelengths as the second narrowband enables the first narrowband and the second narrowband to have the same light absorption coefficient of the hemoglobin.

Furthermore, the first narrowband light is light having a wavelength with a minimum value of the light absorption coefficient of the hemoglobin.

The minimum value is a local smallest value of the light absorption characteristics of the hemoglobin. When the light absorption coefficients of the hemoglobin are the same in the first narrowband and the second narrowband, the wavelength with the minimum value of the light absorption coefficient of the hemoglobin may be set as the first narrowband.

Furthermore, the first narrowband light is light having a wavelength of 500 nm. The second narrowband light is light having a wavelength of 530 nm.

FIG. 11 illustrates a case where the first narrowband has the wavelength of 500 nm and the second narrowband has the wavelength of 530 nm. This is an example of a case where the wavelength with the minimum value of the light absorption coefficient of the hemoglobin is set as the first narrowband. The first narrowband preferably belongs to the green wavelength band to generate the NBI image. The present embodiment can meet this requirement.

The endoscope apparatus 12 in accordance with the present embodiment may have a configuration described below. That is, the processing section 300 includes a memory configured to store information, and a processor configured to operate based on the information stored in the memory. The information includes, for example, a program and various data. The light source 610 emits the illumination light including the first wavelength band light, the first narrowband light, and the second narrowband light. The imaging section 200 captures the first image, the first narrowband image, and the second narrowband image. The processor performs a scattering characteristics information acquisition process and an image generation process. The scattering characteristics information acquisition process acquires the scattering characteristics information based on the comparison result between the first narrowband image and the second narrowband image. The image generation process generates the observation image using the first image, the first narrowband image, and the scattering characteristics information.

The processor may have functions of sections each implemented by individual hardware, or the functions of sections each implemented by integrated hardware, for example. For example, the processor may include hardware, and the hardware may include at least one of a circuit that processes a digital signal and a circuit that processes an analog signal. For example, the processor may include one or more circuit devices mounted on a circuit board, or one or more circuit elements. The circuit device is an integrated circuit (IC), for example. The circuit element is a resistor or a capacitor, for example. The processor may be a central processing unit (CPU), for example. However, the processor is not limited to the CPU, but various other processors such as a graphics processing unit (GPU) or a digital signal processor (DSP) may also be used. The processor may be a hardware circuit that includes an application specific integrated circuit (ASIC), The processor may include an amplifier circuit, a filter circuit, or the like that processes an analog signal. The memory may be a semiconductor memory such as a static random-access memory (SRAM) or a dynamic random-access memory (DRAM), or may be a register. The memory may be a magnetic storage device such as a hard disk drive (HDD), or may be an optical storage device such as an optical disc device. For example, the memory stores a computer-readable instruction, and the processor performs the instruction to implement the function of each section of the processing section 300 as a process. The instruction may be an instruction set that is included in a program, or may be an instruction that instructs the hardware circuit included in the processor to operate. The memory corresponds to a storage section 320 in FIG. 3, for example. The processing section 300 includes sections such as a control section 340, an observation mode switching section 342, a focal distance control section 344, a calculation section 360, a scattering characteristics information acquisition section 361, an observation information acquisition section 362, an image generation section 363, a highlighting amount control section 364, a highlighting processing section 365, and an observation image generation section 366.

The sections of the processing section 300 in accordance with the present embodiment may be implemented as modules of a program operating on the processor. For example, the scattering characteristics information acquisition section 361 is implemented as a scattering characteristics information acquisition processing module, and the image generation section 363 is implemented as an image generation processing module.

Furthermore, the program implementing the processes performed by the sections of the processing section 300 in accordance with the present embodiment can be stored, for example, in a computer-readable information storage medium. The information storage medium can be implemented by an optical disk, a memory card, a HDD, or a semiconductor memory, for example. The semiconductor memory is, for example, a read-only memory (ROM). The processing section 300 performs various processes in accordance with the present embodiment based on the program stored in the information storage medium. That is, the information storage medium stores the program causing a computer to function as the sections of the processing section 300. The computer is a device including an input device, a processing section, a storage section, and an output section. The program causes the computer to execute the processes of the sections of the processing section 300.

2. Detailed Configuration Example

Figure 3:
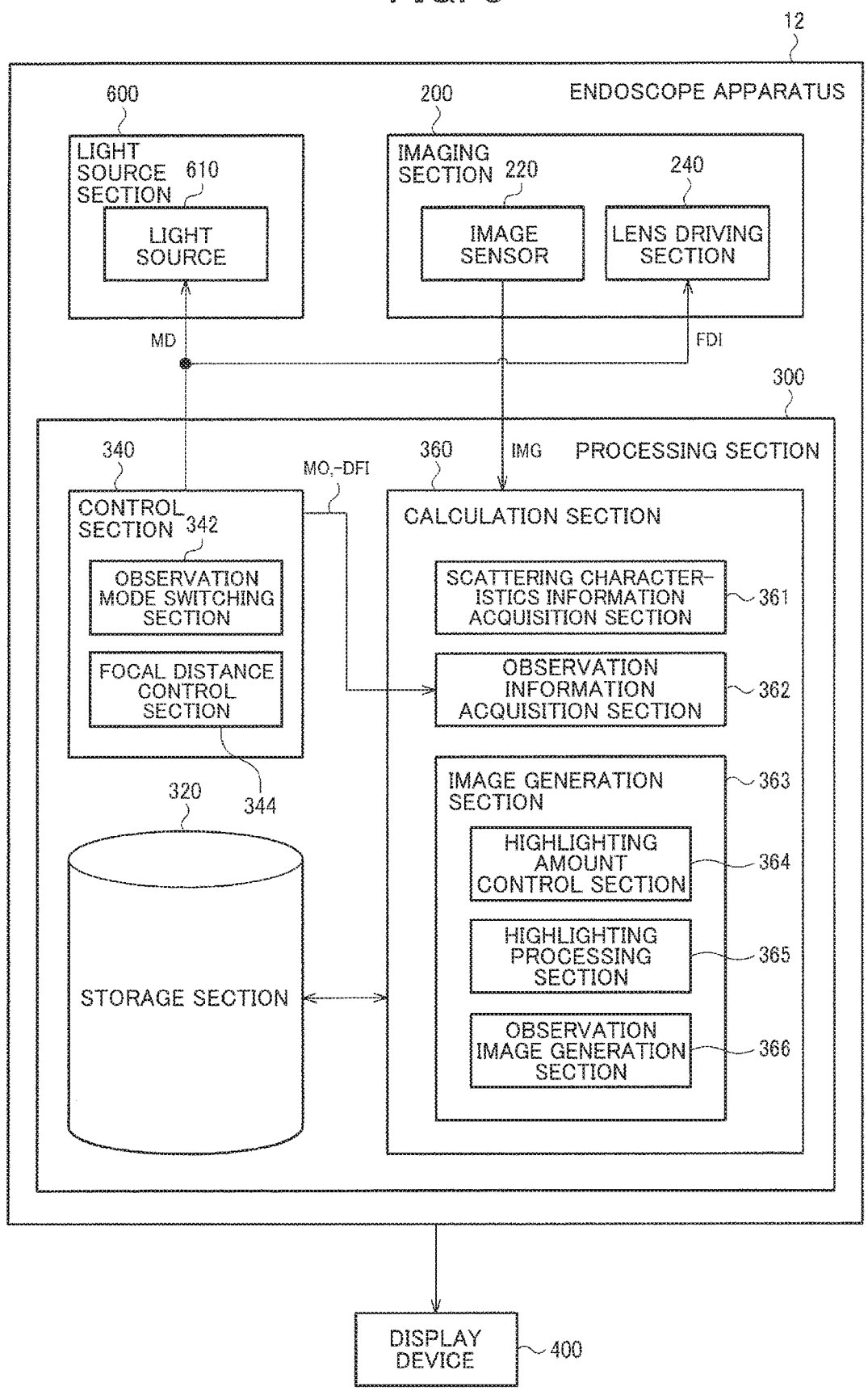
FIG. 3 is a detailed configuration example of the endoscope apparatus.

FIG. 3 is a detailed configuration example of the endoscope apparatus 12. The endoscope apparatus 12 includes the imaging section 200, the processing section 300, and a light source section 600. The light source section 600 is also referred to as an illumination device.

The light source section 600 includes the light source 610 configured to emit the illumination light. The light source 610 is a light-emitting diode (LED), a laser, a xenon lamp, or the like, for example. When a light source having a wide band such as the xenon lamp is used, the light source section 600 may include an optical filter allowing the narrowband light to pass through. When NBI is used, the illumination light is made to enter the optical filter to generate the narrowband light. The illumination light is guided by a light guide (not illustrated) and the guided illumination light is emitted on the object.

The imaging section 200 includes an image sensor 220, and a lens driving section 240. The imaging section 200 also includes an objective lens. The imaging section 200 and the light guide are included in the scope, and the scope is inserted into tissue. As a result, the inside of the tissue is illuminated and imaged. The image sensor 220 captures an object image formed by the objective lens and outputs image data. The objective lens includes a focus lens. The lens driving section 240 drives the focus lens to change a focus position of the objective lens. The lens driving section 240 is an actuator such as a motor.

As for an imaging method, the frame sequential method described below can be assumed. That is, the light source section 600 sequentially emits R light, G light, and B light, and the imaging section 200 sequentially captures an R image, a G image, and a B image. Then, the R image, G image, and B image are combined to obtain the white light image. In addition, the light source section 600 sequentially emits the narrowband light NB, narrowband light NG1, and narrowband light NG2, and the imaging section 200 sequentially captures the NB image, NG1 image, and NG2 image. The narrowband light NG1 and the narrowband light NG2 are the narrowband light having the same light absorption coefficient of the hemoglobin. Details will be described later referring to FIG. 4. The NB image and the NG1 image are combined to obtain the NBI image. As will be described later, the scattering characteristics information is acquired based on the NG1 image and the NG2 image. As will be described later referring to FIG. 7, when an image sensor of a Bayer type is used, another imaging method can be used.

The processing section 300 performs signal processing including image processing and a control of the endoscope apparatus 12. The processing section 300 includes the control section 340, the calculation section 360, and the storage section 320. The control section 340 is also referred to as a controller, and is a control circuit, for example. The calculation section 360 is a calculation circuit, for example. Alternatively, the control section 340 and the calculation section 360 may be implemented by the processor.

The control section 340 controls sections in the endoscope apparatus 12. The control section 340 includes the observation anode switching section 342 configured to switch the observation mode, and the focal distance control section 344 configured to control the focal distance of the objective lens.

The focal distance control section 344 is also referred to as a focus control section. The observation mode switching section 342 sets the observation mode to either the white light mode or the NBI mode. For example, a user operates a button or the like to set the observation mode, and the observation mode switching section 342 outputs a mode control signal MD for instructing the set observation mode. The light source 610 controls the illumination light based on the mode control signal MD.

The focal distance control section 344 outputs a focus control signal FDI for controlling the focal distance of the objective lens. For example, the user operates a dial or the like to set the focal distance, and the focal distance control section 344 outputs the focus control signal FDI for instructing the set focal distance. The lens driving section 240 drives the focus lens based on the focus control signal FDI.

The calculation section 360 generates the observation image, and highlights the observation image based on the scattering characteristics. The calculation section 360 includes the scattering characteristics information acquisition section 361, the observation information acquisition section 362, and the image generation section 363. The image generation section 363 includes the highlighting amount control section 364, the highlighting processing section 365, and the observation image generation section 366.

The scattering characteristics information acquisition section 361 acquires the scattering characteristics information of the object based on the NBI image. The scattering characteristics information is an image showing the scattering characteristics. The pixel value of each pixel of the image is a value indicating the scattering characteristics of the object. The image is referred to as the scattering characteristics image. The scattering characteristics image is generated based on the difference in the scattering characteristics between the cancer and the area other than the cancer. The pixel value is relatively higher in the area of the cancer than in the area other than the cancer.

The observation information acquisition section 362 acquires observation information based on the mode control signal MD and the focus control signal FDI. Specifically, the observation information acquisition section 362 acquires the observation information indicating which one of the white light mode and the NBI mode is set based on the mode control signal MD. In addition, the observation information acquisition section 362 acquires the observation information indicating which one of the screening observation and the magnifying observation is being performed based on the focus control signal FDI. The screening observation is an observation method for screening presence or absence of a lesion by moving the scope. In the screening observation, the focal distance is set to a focal distance allowing deep focus, that is, a focal distance on a far point side that is farther than a focal distance in the magnifying observation. The magnifying observation is an observation method for carefully examining the object by bringing the scope closer to the object to magnify the object. In the magnifying observation, the focal distance is set to a focal distance on a near point side. The observation information acquisition section 362 determines which one of the screening observation and the magnifying observation is being performed based on the focal distance indicated by the focus control signal FDI.

The image generation section 363 generates the observation image from the images captured by the imaging section 200, and outputs the observation image to a display device 400. The display device 400 is, for example, a liquid crystal display device. The display device 400 may be included in the endoscope apparatus 12. The observation image is an image displayed to the user, and is also referred to as a display image. The image generation section 363 controls the image generation process of the observation image or the highlighting process of the observation image based on the scattering characteristics information and the observation information. The image generation section 363 generates the observation image from the images captured in white light illumination when the observation mode is in the white light mode, and generates the observation image based on the images captured in narrowband light illumination when the observation mode is in the NBI mode. The image generation section 363 includes the highlighting amount control section 364, the highlighting processing section 365, and the observation image generation section 366.

The highlighting amount control section 364 controls the highlighting amount of the highlighting process based on the scattering characteristics information. That is, the highlighting amount control section 364 controls the highlighting amount in each pixel in the captured image based on the pixel value of the corresponding pixel in the scattering characteristics image. The observation image generation section 366 generates the observation image from the captured images. The observation image generation section 366 combines the R image, G image, and B image to generate the observation image in the white light mode, and combines the NB image and NG1 image to generate the observation image in the NBI mode. The highlighting processing section 365 performs the highlighting process on the observation image based on the highlighting amount set by the highlighting amount control section 364, and outputs the resultant observation image after the highlighting process to the display device 400. Furthermore, the highlighting processing section 365 may control the content of the highlighting process based on the scattering characteristics information or the observation information.

The storage section 320 is a working memory of the calculation section 360, for example. Alternatively, the storage section 320 stores parameters used for various processes such as the highlighting process. Alternatively, when the calculation section 360 is the processor, the storage section 320 stores a program executed by the processor. The storage section 320 is, for example, a semiconductor memory, or a HDD.

3. Operation of Detailed Configuration Example

Operation performed by the endoscope apparatus 12 illustrated in FIG. 3 is described below. First of all, a method for distinguishing the early-stage cancer from the inflammation area in NBI observation is described in principle in accordance with the present embodiment.

The cell nucleus in the mucosa is enlarged in the early-stage cancer. On the other hand, the cell nucleus is not enlarged in normal mucosa or the inflammation area. Accordingly, when the cell nucleus is used as the scatterer, the scattering characteristics differ between the early-stage cancer and the inflammation. That is, the scattering coefficients with respect to the illumination light differ between the early-stage cancer and the inflammation depending on a size of the scatterer.

FIG. 4 is a graph illustrating the narrowband light used in the NBI observation in accordance with the present embodiment. As illustrated in FIG. 4, the narrowband light NG1 and the narrowband light NG2 are emitted on the object as the narrowband light included in the green wavelength band. The narrowband light NG1 has the wavelength of 540 nm. and the narrowband light NG2 has the wavelength of 570 nm. The wavelengths of the narrowband light NG1 and the narrowband light NG2 are not limited to these values, but may be of any value as long as the wavelengths have the same light absorption coefficient of the hemoglobin. The light absorption coefficients of the narrowband light NG1 and the narrowband light NG2 do not need to be completely the same, but may be approximately the same. For example, the light absorption coefficients may differ by a few percent.

The image of the object illuminated by the narrowband light NG1 is referred to as the NG1 image, and the image of the object illuminated by the narrowband light NG2 is referred to as the NG2 image. The ratio between the pixel value in the NG1 image and the pixel value in the NG2 image is obtained for each pixel, and the scattering characteristics image having these ratios as the pixel values is obtained. The scattering characteristics image corresponds to the scattering characteristics information. Since the light absorption coefficients of the hemoglobin are the same at the wavelengths of the narrowband light NG1 and the narrowband light NG2, the influence of the hemoglobin can be cancelled by obtaining the ratio. That is, information about the scattering characteristics of the object remains in the scattering characteristics information.

Figure 5:
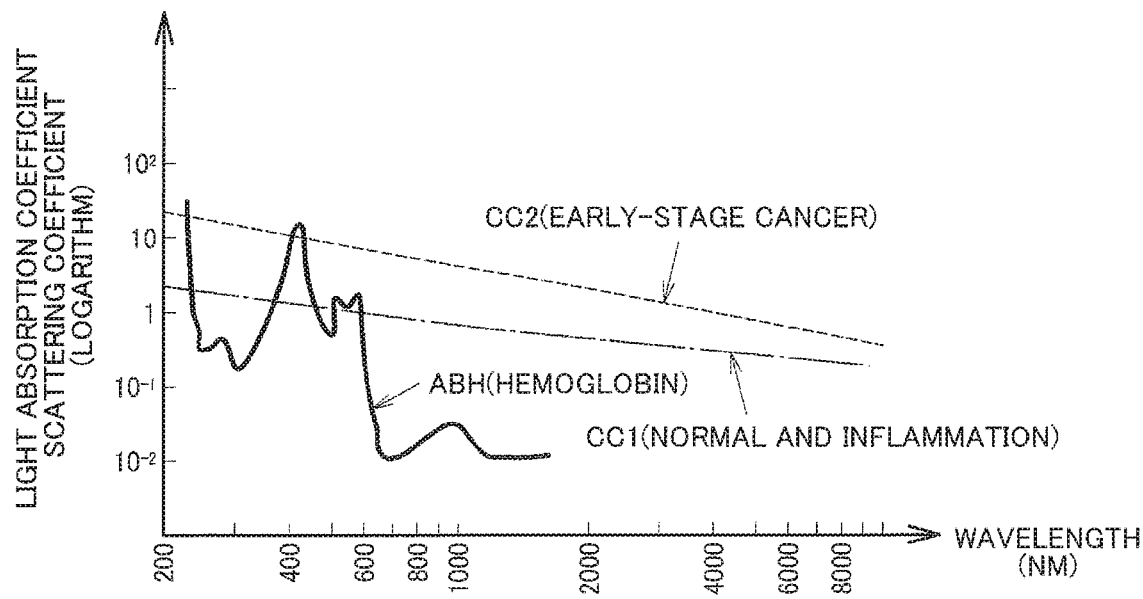
FIG. 5 is a graph illustrating light absorption characteristics of hemoglobin and scattering characteristics of an object.

FIG. 5 illustrates the light absorption characteristics of the hemoglobin and the scattering characteristics of the object. Light absorption characteristics ABH of the hemoglobin is the same as those illustrated in FIG. 4. The light absorption characteristics ABH do not depend on the object and thus do not change. CC1 represents the scattering characteristics of the normal mucosa and the inflammation area. CC2 represents the scattering characteristics of the early-stage cancer. The Mie scattering is dominant in the tissue. The Mie scattering is scattering caused by a scatterer having a size approximately equivalent to a wavelength of light. Intensity of scattering light in the Mie scattering depends on the wavelength of the light and a particle size of the scatterer. The scatterer is the cell nucleus. The scattering light becomes more intense as the particle size of the cell nucleus becomes larger. The scattering light also becomes more intense as the wavelength of the light is shorter. The cell nucleus of the early-stage cancer is larger than the cell nucleuses of the normal mucosa and the inflammation area. Thus, in comparison at the same wavelength, the scattering coefficient of the scattering characteristics CC2 is larger than the scattering coefficient of the scattering characteristics CC1.

FIG. 6 is a graph illustrating a method for acquiring the scattering characteristics information. As illustrated in FIG. 6, the ratio of the pixel value in the NG1 image to the pixel value in the NG2 image is obtained for each pixel. The scattering characteristics image is a ratio image including these ratios. The brightness of the ratio image, i.e., the pixel value, is the change amount between the scattering coefficient at the wavelength of 540 nm and the scattering coefficient at the wavelength of 570 nm. The change amount corresponds to the gradients $\Delta s1$ and $\Delta s2$ in FIG. 6. As described above, since the scattering coefficient is larger in the early-stage cancer than in the normal mucosa and the inflammation area, the gradient $\Delta s2$ is larger than the gradient $\Delta s1$. That is, the early-stage cancer is brighter than the normal mucosa and the inflammation area in the scattering characteristics image.

Performing the highlighting process on the image based on this scattering characteristics information enables easy identification between the early-stage cancer and the inflammation in the observation image. That is, since the brighter area in the scattering characteristics image is highlighted by a larger highlighting amount, the early-stage cancer can be more highlighted than the normal mucosa and the inflammation area.

Details of the processes performed by the endoscope apparatus 12 are described below. FIG. 7 is a flowchart illustrating procedures of the processes.

As indicated by a step S10, the imaging section 200 acquires the images. That is, the imaging section 200 acquires the NB image, NG1 image, and NG2 image in the NBI mode. The imaging section 200 also acquires the white light image in the white light mode. The imaging section 200 may acquire both the NBI image and the white light image. The imaging section 200 takes a video, and an image captured in each frame in the video corresponds to the image described herein.

With a monochrome image sensor, light having the wavelengths of 410, 540, and 570 nm is sequentially emitted. The imaging section 200 captures the image at each timing of the light emission. The image sensor may be an image sensor of the Bayer type having an RGB color filter, or an image sensor of complementary colors having a cyan-magentayellow-green (CyMgYeG) color filter. In this case, the light having the wavelength of 540 nm is emitted at a first timing, and the light having the wavelengths of 410 and 570 nm is emitted in a following second timing. The imaging section 200 captures the images at respective timings. The image sensor may be an image sensor having three types of color filters each corresponding to the wavelength of each narrowband light. In this case, the light in three bands is simultaneously emitted, and the imaging section 200 captures the images at this timing. The wavelengths of the light may be the wavelengths described later referring to FIGS. 10 and 11.

Next, as indicated by a step S11, the scattering characteristics information acquisition section 361 acquires the change amount between the scattering coefficient at the wavelength of 540 nm and the scattering coefficient at the wavelength of 570 nm based on the NG1 image and the NG2 image. As described referring to FIG. 4, the light absorption coefficients of the hemoglobin are the same at the wavelengths 540 and 570 nm, Since the hemoglobin is a major light absorbing body in the tissue, the NG1 image and the NG2 image become brighter as the intensity of the scattering light is higher. In accordance with the present embodiment, the scattering characteristics information acquisition section 361 acquires the change amount of the scattering characteristics by calculating the ratio between the NG1 image and the NG2 image. Specifically, the ratio is calculated by the formulas (1) and (2) below.

$$PSI=(PNG1/PNG2)/AVSI \qquad (1)$$

$$ASI=AVNG1/AVNG2 \qquad (2)$$

PSI represents a pixel value of the scattering characteristics image. PNG1 represents a pixel value of the NG1 image, and PNG2 represents a pixel value of the NG2 image. The pixel value is a pixel value of a pixel at a position (x, y). Calculation is performed by the formula (1) for each position (x, y) to acquire the scattering characteristics image. AVSI represents an average value of the scattering characteristics information. AVNG1 represents an average value of the pixel values in the whole NG1 image, and AVNG2 represents an average value of the pixel values in the whole NG2 image.

When PSI is lower than one (PSI<1) in a solution of the formula (1) above, PSI may be clipped by setting PSI to one (PS=1). PSI of the cancer is generally assumed to be higher than one (PSI>1), and PSI of normal tissue is assumed to be nearly equal to one (PSI≈1). PSI lower than one (PSI<1) is out of an assumption range. Thus, clipping PSI with one as a lowest value (PSI=1) stabilizes the color of the highlighted image.

The scattering characteristics information acquisition section 361 may perform positioning before acquiring the scattering characteristics information. When the images are captured at respective wavelengths in time series, the position shift occurs between the images. The scattering characteristics information acquisition section 361 positions the NG1 image and the NG2 image using block matching or the like, and acquires the scattering characteristics information using the NB image and the NG1 image after the positioning. As a result, robustness with respect to the motion of the object is improved.

Furthermore, the scattering characteristics information acquisition section 361 may perform the brightness correction before acquiring the scattering characteristics information. When the images are captured at respective wavelengths in time series, the brightness of the NG1 image and the NG2 image may differ due to the position shift. When the images are simultaneously captured, the brightness of the NG1 image and the NG2 image may differ due to a difference in quantity of light between the narrowband light NG1 and the narrowband light NG2. The scattering characteristics information acquisition section 361 equalizes average brightness in the whole images, and acquires the scattering characteristics information using the NB image and the NG1 image after the brightness equalization.

Furthermore, the scattering characteristics information acquisition section 361 may perform the noise reduction process before acquiring the scattering characteristics information. That is, the scattering characteristics information acquisition section 361 performs the noise reduction process on the NG1 image and the NG2 image, and acquires the scattering characteristics information using the NG1 image and the NG2 image after the noise reduction process. Alternatively, since the cancer has a predetermined area, the scattering characteristics information acquisition section 361 extracts low frequency components of the images from the NG1 image and the NG2 image. That is, the scattering characteristics information acquisition section 361 performs a low pass filter process for a band corresponding to a size of the cancer on the NG1 image and the NG2. image. Then, the scattering characteristics information acquisition section 361 acquires the scattering characteristics information from the extracted low frequency components.

Furthermore, the scattering characteristics information acquisition section 361 may extract the scattering characteristics information from a difference as indicated by the formula (3) below. When PSI is lower than one (PSI<1) in a solution of the formula (3) below, PSI may be clipped by setting PSI to one (PS=1). Clipping PSI with one as the lowest value (PSI=1) can stabilize the color of the highlighted image.

$$PSI=1+(PNG1-PNG2)/AVSI \qquad (3)$$

Furthermore, the scattering characteristics information acquisition section 361 may acquire the scattering characteristics information from the images at three wavelengths as indicated by formulas (4) and (5) below.

$$PSI=(PNG1/PNG2)/AVSI+(PNG3/PNG1)/AVSI' \qquad (4)$$

$$AVSI'=AVNG3/AVNG1 \qquad (5)$$

PNG3 represents a pixel value of an NG3 image, and the NG3 image is an image captured when third narrowband light is emitted on the object. The third narrowband light has a wavelength of 450 nm, for example, and the light absorption coefficient of the hemoglobin is the same as that of the narrowband light NG1 and the narrowband light NG2. AVNG3 represents an average value of the pixel values in the whole NG3 image. Using the ratio of PNG3/PNG1 together improves noise resistance and extraction accuracy of the scattering characteristics.

Furthermore, the scattering characteristics information acquisition section 361 may perform the noise reduction process after acquiring the scattering characteristics information. That is, the scattering characteristics information acquisition section 361 performs the noise reduction process on the scattering characteristics image, and outputs a resultant scattering characteristics image after the process as final scattering characteristics information. Since the scattering characteristics information uses the ratio between the pixel values of the two images, the scattering characteristics information tends to include much noise. Performing the noise reduction process can improve the noise resistance.

Furthermore, the scattering characteristics information acquisition section 361 may perform the binarization process after acquiring the scattering characteristics information. That is, the scattering characteristics information acquisition section 361 performs the binarization process on the scattering characteristics image, and outputs a resultant scattering characteristics image after the process as the final scattering characteristics information. For example, the scattering characteristics information acquisition section 361 averages the pixel values in the whole scattering characteristics image, and binarizes the pixel values of the scattering characteristics image with an average value as a threshold value. As a result, only an area having a pixel value higher than the threshold value is highlighted. The area having the pixel value higher than the threshold value is an area assumed to be the cancer, and thus the area of the cancer can be clearly highlighted.

Next, as indicated by a step S12, the observation information acquisition section 362 acquires the observation information. That is, the observation information acquisition section 362 acquires the information about which one of the NBI mode and the white light mode is set based on the mode control signal MD. The observation information acquisition section 362 also acquires the information about which one of the screening observation and the magnifying observation is being performed based on the focus control signal FDI. In addition, the observation information acquisition section 362 acquires the motion amount of the images by a matching process between the frames or the like. Since the observation information is acquired and the highlighting process, described later, is controlled based on the observation information, highlighting can be suppressed in a scene not requiring highlighting. Since the noise is increased by highlighting, the noise can be suppressed in the scene not requiring highlighting.

Next, as indicated by a step S13, the highlighting amount control section 364 controls the highlighting amount based on the scattering characteristics information. Specifically, the highlighting amount control section 364 corrects the scattering characteristics information extracted in the step S11. The highlighting amount control section 364 multiplies the pixel value of the scattering characteristics image by a coefficient to correct the scattering characteristics information. The coefficient is referred to as a highlighting amount control coefficient. The highlighting amount control section 364 changes the highlighting amount control coefficient for each pixel or area to control the highlighting amount. The highlighting processing section 365, described later, performs the highlighting process using the scattering characteristics information after the correction.

FIG. 8 illustrates a first characteristics example of the highlighting amount control coefficient. FIG. 9 illustrates a second characteristics example of the highlighting amount control coefficient. Although it is preferable to suppress highlighting in an area not requiring highlighting, discontinuous control between presence and absence of highlighting creates an unnatural boundary between the presence and absence of highlighting. Thus, the highlighting amount is continuously controlled. In FIG. 8, when the index is lower than a threshold value, the highlighting amount control coefficient becomes larger as the index becomes higher. When the index is higher than the threshold value, the highlighting amount control coefficient is set to one. When the index is lower than the threshold value, the highlighting amount control coefficient is proportional to the index as indicated by A1. However, the characteristics of the highlighting amount control coefficient are not limited to this, but may be any characteristics such as a sigmoid function or the like as indicated by A2 and A3. In FIG. 9, when the index is lower than a threshold value, the highlighting amount control coefficient is set to one. When the index is higher than the threshold value, the highlighting amount control coefficient becomes smaller as the index becomes higher. When the index is higher than the threshold value, the highlighting amount control coefficient is proportional to the index as indicated by B1. However, the characteristics of the highlighting amount control coefficient are not limited to this, but may be any characteristics such as the sigmoid function or the like as indicated by B2 and B3. As will be described later, the characteristics in FIGS. 8 and 9 are used properly depending on types of the indexes.

In FIGS. 8 and 9, a smallest value of the coefficient is set to 0.5 and a largest value of the coefficient is set to 1.0. However, the smallest value and the largest value are not limited to these values. The smallest value may be set to 0.0, for example. No highlighting is applied to a pixel multiplied by 0.0. Thus, the noise can be more suppressed. The largest value may be set to 1.5, for example. Highlighting is more strongly applied to a pixel multiplied by a coefficient larger than one. Thus, a contrast between the cancer and the inflammation can be highlighted.

The highlighting amount control section 364 makes the highlighting amount in the brownish area relatively larger than the highlighting amount in the area other than the brownish area. The cancer and the inflammation are basically brownish areas, and highlighting the area other than the brownish area only increases the noise. Thus, the highlighting amount in the brownish area is made relatively larger.

Specifically, the highlighting amount control section 364 sets the highlighting amount control coefficient based on a ratio of the R pixel value to a pixel value of another color. For example, a ratio of the R pixel value/the G pixel value is used as the index. As illustrated in FIG. 8, the highlighting amount control section 364 makes the highlighting amount control coefficient larger as the index becomes higher. A predetermined value may be set as the threshold value in FIG. 8. Alternatively, an average value of the ratios of the R pixel value/the G pixel value in the whole image may be set as the threshold value. Since the R pixel value in the brownish area is high in both the white light image and the NBI image, the ratio of the R pixel value/the G pixel value becomes high. On the contrary, the ratio of the R pixel value/the G pixel value becomes low in the area other than the brownish area. Thus, using the ratio of the R pixel value/the G pixel value as the index can make the highlighting amount in the brownish area relatively large. The area having a high ratio of the R pixel value/the G pixel value includes a blood vessel area. Accordingly, a ratio of the R pixel value,/the G pixel value after the low pass filter process may be used, for example. As a result, the blood vessel including a high frequency component can be excluded, and only the brownish area including a low frequency component can be extracted.

Furthermore, the highlighting amount control section 364 makes the highlighting amount in a non-tissue area relatively smaller than the highlighting amount in a tissue area. The non-tissue area is, for example, a treatment tool. As illustrated in FIG. 9, using the edge component or a divergence from a reference hue as the index, the highlighting amount control section 364 makes the highlighting amount control coefficient smaller as the index becomes higher.

A case using the edge component as the index is described herein. The non-tissue area such as the treatment tool does not need to be highlighted, and generally includes the edge component larger than the edge component in the tissue area. The highlighting amount control section 364 extracts the edge component from the NBI image or the white light image, and makes the highlighting amount control coefficient larger as the edge component is lager. A predetermined value may be set to the threshold value in FIG. 9. Alternatively, an average value of edge amounts in the whole image may be set to the threshold value.

A case using the divergence from the reference hue as the index is described herein. For example, the highlighting amount control section 364 defines the reference hue on a CbCr plane. The highlighting amount control section 364 performs YCbCr conversion on the white light image or the NBI image, and obtains a difference between a hue and the reference hue for each pixel in a resultant image after the conversion. The highlighting amount control section 364 makes the highlighting amount control coefficient larger as the difference becomes larger. Since the tissue has a red hue, the reference hue corresponding to this red hue is set. A predetermined value may be set to the reference hue. Alternatively, an average value of the hues in the whole image may be set to the reference hue.

Furthermore, the highlighting amount control section 364 makes the highlighting amount smaller when the motion amount between the images is large. When the motion of the object is large, a scene change is presumably occurring. Highlighting during the scene change only increases the noise, and thus highlighting is hardly necessary during the scene change.

Specifically, the highlighting amount control section 364 performs matching between the frames or the like to obtain the motion amount of the images between the frames. Using the motion amount as the index, the highlighting amount control section 364 makes the highlighting amount control coefficient smaller as the index becomes higher, as illustrated in FIG. 9.

Furthermore, the highlighting amount control section 364 makes the highlighting amount smaller when the focal distance of the objective lens is short. When the focal distance of the objective lens is long or intermediate, screening is being performed, and thus highlighting is required. On the contrary, when the focal distance of the objective lens is short, close observation is presumably being performed, and thus highlighting is suppressed. The close observation is also referred to as the magnifying observation. Highlighting during the screening can help to discover a lesion candidate. On the other hand, highlighting during the close observation is not necessary or may be suppressed, since the user closely observes an area that the user determined to see in detail during the screening.

Specifically, the focus control signal FDI is acquired as the observation information. Then, using the focal distance indicated by the focus control signal FDI as the index, the highlighting amount control section 364 makes the highlighting amount control coefficient smaller as the index becomes lower, as illustrated in FIG. 8.

Although five methods for controlling the highlighting amount are described above, only one or all of the five methods may be used, or some of the five methods may be combined.

Next, the observation image generation section 366 generates the observation image as indicated by a step S14 in FIG. 7. The observation image generation section 366 sets the NB image captured in the blue narrowband light NB as the G image and the B image, and sets the NG1 image captured in the green narrowband light NG1 as the R image. Then, the observation image generation section 366 combines the R image, G image, and B image to generate the NBI image in the NBI mode. The NBI image is the observation image in the NBI mode.

Alternatively, the observation image may be generated with a red image. That is, the light source emits light having a wavelength of 630 nm, and the imaging section 200 captures an image at a timing when the light is emitted on the object. This image is referred to as a second image or an NR image. The observation image generation section 366 sets the NR image as the R image, the NG1 image as the G image, and the NB image as the B image. Then, the observation image generation section 366 combines the R image, G image, and B image to generate the observation age. As a result, color reproduction equivalent to the white light mode can be implemented. In addition, performing the highlighting process, described later, on the observation image can highlight the area of the cancer in a color different from the color of the inflammation area.

Next, as indicated by a step S15 in FIG. 7, the highlighting processing section 365 performs the highlighting process on the observation image generated in the step S14, and outputs a resultant image after the highlighting process to the display device 400 as the final observation image. For example, the highlighting process is defined by formulas (6) to (8) below.

$$CHR'=CHR \tag{6}$$

$$CHG'=CHG \times EAM \tag{7}$$

$$CHB'=CHB \tag{8}$$

CHR represents the R channel (R pixel value) of the observation image generated in the step S14, CHG represents the G channel (G pixel value) of the observation image generated in the step S14, and CHB represents the B channel (B pixel value) of the observation image generated in the step S14. CHR' represents the R channel (R pixel value) of the image after the highlighting process, CHG' represents the G channel (G pixel value) of the image after the highlighting process, and CHB' represents the B channel (B pixel value) of the image after the highlighting process. EAM represents the pixel value of the scattering characteristics image corrected in the step S13. That is, EAM is the pixel value obtained by multiplying PSI in the formula (1) above by the highlighting amount control coefficient.

The pixel value of the scattering characteristics image in the area of the early-stage cancer is larger than one, and thus the G pixel value is raised by the highlighting process. As a result, the area of the early-stage cancer has a yellow (Ye) tone, whereby the area can be distinguished from the brownish area of other than the cancer. The highlighting process is not limited to the formulas (6) to (8) above. For example, EAM may multiplied to the pixel value of the B channel. In this case, the area of the early-stage cancer has a magenta (Mg) tone. The channel to be highlighted may be changed between the white light mode and the NBI mode.

Next, a modification example of the highlighting process is described. The highlighting amount is controlled in the step S13 in FIG. 7, however, the highlighting amount may be controlled in the step S15. That is, the highlighting processing section 365 may blend the highlighted image with an original image to suppress the highlighting amount in the step S15.

Specifically, a possible range of a blend ratio is 0≤blend ratio≤1. The highlighting processing section 365 controls the blend ratio based on the indexes described in the step S13. Specifically, the highlighting processing section 365 makes the blend ratio higher as the ratio of the R pixel value/the G pixel value is higher. Furthermore, the highlighting processing section 365 makes the blend ratio lower as the edge component is larger. Furthermore, the highlighting processing section 365 makes the blend ratio lower as the divergence between the hue and the reference hue is larger. Furthermore, the highlighting processing section 365 makes the blend ratio lower as the motion amount between the frames is larger. Furthermore, the highlighting processing section 365 makes the blend ratio lower as the focal distance is shorter.

The highlighting process is defined by formulas (9) to (11) below. BRT represents the blend ratio. In the formula (10) below, a first term on the right side represents the highlighted image highlighted by the highlighting amount EAM and a second term on the right side represents the observation image before being highlighted. As the blend ratio BRT is higher, a ratio of the highlighted image highlighted by the highlighting amount EAM becomes higher. As the blend ratio BRT is lower, a ratio of the observation image before being highlighted becomes higher.

$$CHR'=CHR \tag{9}$$

$$CHG'=CHG \times EAM \times BRT + CHG \times (1-BRT) \tag{10}$$

$$CHB'=CHB \tag{11}$$

Next, a modification example of the narrowband light is described. FIG. 10 is a first modification example of the narrowband light. FIG. 10 illustrates the narrowband light NG2 having a wavelength of 450 nm. The wavelength of 450 nm belongs to the blue wavelength band. The narrowband light NG1 has a wavelength of 540 nm as in FIG. 4. The light absorption coefficient of the hemoglobin at the wavelength of 450 nm is the same as the light absorption coefficient of the hemoglobin at the wavelength of 540 nm.

FIG. 11 is a second modification example of the narrowband light. FIG. 11 illustrates the narrowband light NG1 and the narrowband light NG2 both having the wavelengths different from the wavelengths in FIG. 4. The narrowband light NG1 has a wavelength of 500 nm, and the narrowband light NG2 has a wavelength of 530 nm. The wavelengths of 500 and 530 nm belong to the green wavelength band. The light absorption coefficients of the hemoglobin at the wavelengths of 500 and 530 nm are the same.

4. Surgery Support System

The endoscope apparatus is assumed to be a type that the control device and the scope are connected to allow the user to operate the scope to take a video of the inside of a body. However, the present disclosure is not limited to this. As an endoscope apparatus applied with the present disclosure, a surgery support system using a robot can be assumed, for example.

For example, the surgery support system includes a control device, a robot, and a scope. The scope is, for example, a rigid scope. The control device is a device configured to control the robot. That is, the user operates an operation section of the control device to move the robot through which to perform surgery on a patient. The user also operates the operation section of the control device to manipulate the scope via the robot and capture images of a surgical region. The control device includes the processing section 300 in FIG. 2 or 3. The user operates the robot while watching the images displayed on a display device by the processing section 300. The present disclosure can be applied to the control device in such a surgery support system. The control device may be embedded in the robot.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in an place in the specification and the drawings.

What is claimed is:

1. An endoscope apparatus comprising:
    a light source configured to emit illumination light including light in a first wavelength band included in a blue wavelength band, light in a first narrowband included in a green wavelength band, and light in a second narrowband having a same light absorption coefficient of hemoglobin as that of the light in the first narrowband;
    an imager configured to capture an image of return light from an object that receives the illumination light so as to acquire a first image that is an image of the object in the first wavelength band, a first narrowband image that is an image of the object in the first narrowband, and a second narrowband image that is an image of the object in the second narrowband; and
    a processor including hardware, the processor being configured to implement:
        acquiring scattering characteristics information that is information about scattering characteristics of the object based on a comparison result between the first narrowband image and the second narrowband image; and
        generating an observation image using the first image, the first narrowband image, and the scattering characteristics information.

2. The endoscope apparatus as defined in claim 1, wherein the processor acquires a change amount between the scattering characteristics in the first narrowband and the scattering characteristics in the second narrowband as the scattering characteristic information.

3. The endoscope apparatus as defined in claim 2, wherein the scattering characteristics are scattering characteristics of a cell nucleus included in the object.

4. The endoscope apparatus as defined in claim 2, wherein the processor acquires the scattering characteristics information based on a ratio between a pixel value of the first narrowband image and a pixel value of the second narrowband image.

5. The endoscope apparatus as defined in claim 2, wherein the processor acquires the scattering characteristics information based on a subtraction result between a pixel value of the first narrowband image and a pixel value of the second narrowband image.

6. The endoscope apparatus as defined in claim 2, wherein the processor
acquires a scattering characteristics image having a pixel value equivalent to the change amount as the scattering characteristic information,
performs a correction process on the scattering characteristics image thus acquired, and
generates the observation image using the scattering characteristics image after the correction process.

7. The endoscope apparatus as defined in claim 1, wherein the processor
generates the observation image from the first image and the first narrowband image, and
performs a highlighting process on the observation image by a highlighting amount controlled in accordance with hemoglobin content.

8. The endoscope apparatus as defined in claim 7, wherein the processor makes the highlighting amount larger in an area having higher hemoglobin content in the observation image.

9. The endoscope apparatus as defined in claim 1, wherein the processor
generates the observation image from the first image and the first narrowband image, and
performs a highlighting process on the observation image by a highlighting amount or with content controlled in accordance with an observation scene.

10. The endoscope apparatus as defined in claim 9, wherein the processor generates the observation image from the first image and the first narrowband image, and performs the highlighting process with first content on the observation image in a first mode,
whereas the processor generates a second observation image, and performs the highlighting process with second content different from the first content on the second observation image in a second mode, the second observation image being an image of the object in a wavelength band of white light.

11. The endoscope apparatus as defined in claim 9, wherein
the processor makes the highlighting amount smaller as a motion amount of the object is larger.

12. The endoscope apparatus as defined in claim 9, wherein
the processor makes the highlighting amount smaller in magnifying observation than in observation other than the magnifying observation, the magnifying observation magnifying the object for imaging.

13. The endoscope apparatus as defined in claim 9, wherein
the processor makes the highlighting amount smaller in an area where an object other than tissue is imaged in the observation image than in an area where the tissue is imaged in the observation image.

14. The endoscope apparatus as defined in claim 1, wherein
the processor performs a highlighting process on a specific channel image out of a plurality of channel images included in the observation image.

15. The endoscope apparatus as defined in claim 1, wherein
the processor performs a color conversion process on the observation image based on the scattering characteristics information.

16. The endoscope apparatus as defined in claim 1, wherein
the light in the first narrowband is light having a wavelength with a maximum value of the light absorption coefficient of the hemoglobin.

17. The endoscope apparatus as defined in claim 16, wherein
the light in the first narrowband is light having a wavelength of 540 nm, and
the light in the second narrowband is light having any one of wavelengths of 570 and 450 nm.

18. The endoscope apparatus as defined in claim 1, wherein
the light in the first narrowband is light having a wavelength with a minimum value of the light absorption coefficient of the hemoglobin.

19. The endoscope apparatus as defined in claim 18, wherein
the light in the first narrowband is light having a wavelength of 500 nm, and
the light in the second narrowband is light having a wavelength of 530 nm.

20. An operating method of an endoscope apparatus comprising:
emitting illumination light including light in a first wavelength band included in a blue wavelength band, light in a first narrowband included in a green wavelength band, and light in a second narrowband having a same light absorption coefficient of hemoglobin as that of the light in the first narrowband;
capturing an image of return light from an object that receives the illumination light so as to acquire a first image that is an image of the object in the first wavelength band, a first narrowband image that is an image of the object in the first narrowband, and a second narrowband image that is an image of the object in the second narrowband;
acquiring scattering characteristics information that is information about scattering characteristics of the object based on a comparison result between the first narrowband image and the second narrowband image; and
generating an observation image using the first image, the first narrowband image, and the scattering characteristics information.

* * * * *